(12) United States Patent
Rudy, Jr. et al.

(10) Patent No.: US 7,291,121 B2
(45) Date of Patent: **\*Nov. 6, 2007**

(54) CERVICAL IMMOBILIZING DEVICE

(75) Inventors: Ronald M. Rudy, Jr., Boynton Beach, FL (US); Freddy T. Lee, Boynton Beach, FL (US); Thomas Murphy, Boynton Beach, FL (US); Sanjay H. Parikh, Finksburg, MD (US)

(73) Assignee: Ambu Inc., Glen Burnie, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/171,190

(22) Filed: Jul. 1, 2005

(65) Prior Publication Data

US 2005/0240130 A1    Oct. 27, 2005

Related U.S. Application Data

(63) Continuation-in-part of application No. 10/151,844, filed on May 22, 2002, now Pat. No. 6,913,584, which is a continuation of application No. 09/427,749, filed on Oct. 27, 1999, now Pat. No. 6,398,747.

(51) Int. Cl.
*A61F 5/04* (2006.01)
*A61F 5/055* (2006.01)

(52) U.S. Cl. ............... 602/18; 602/5; 5/632; 5/628; 128/845; 128/DIG. 23

(58) Field of Classification Search ............... 602/5, 602/17, 18; 128/DIG. 23, 845, 846, 869, 128/870; 5/622, 630, 636, 637, 640, 643, 5/632, 628; 2/468
See application file for complete search history.

(56) References Cited

U.S. PATENT DOCUMENTS

| | | | | | |
|---|---|---|---|---|---|
| 4,472,082 | A | * | 9/1984 | Kroling ................. | 405/186 |
| 4,928,711 | A | * | 5/1990 | Williams ................. | 5/628 |
| 4,964,416 | A | * | 10/1990 | Foldesy et al. ........... | 128/842 |
| 5,383,711 | A | * | 1/1995 | Houghteling ............ | 297/397 |
| 5,524,639 | A | * | 6/1996 | Lanier et al. ........... | 5/630 |
| 5,918,335 | A | * | 7/1999 | Han ..................... | 5/655 |
| 5,944,016 | A | * | 8/1999 | Ferko, III ............. | 128/869 |
| 6,158,813 | A | * | 12/2000 | Karash ................. | 297/391 |
| 6,176,549 | B1 | * | 1/2001 | Karash ................. | 297/391 |

(Continued)

*Primary Examiner*—Justine R. Yu
*Assistant Examiner*—Shumaya Ali
(74) *Attorney, Agent, or Firm*—Levy & Grandinetti

(57) ABSTRACT

A cervical immobilizing device includes a pair of arms that can be folded to an upright position to engage and support a patient's head, an actuating device for folding the arms to the supporting position, and a locking device for locking the position of the arms in the folded supporting position. The actuating device is coupled to the outer ends of the arms for folding the arms to an upright position symmetrically and uniformly. In one embodiment, the actuator device is flexible member that passes around a guide to a position which can be gripped by the user. The locking device can be a cinching, ratcheting or clamping device, or a combination thereof, on the actuator device. In one embodiment, the folding arms include a coupling device for coupling the arms to a base in a sliding arrangement to enable the arms to slide along the base to a folded position. A blank is also disclosed that can be folded to form the cervical immobilizing device.

15 Claims, 14 Drawing Sheets

U.S. PATENT DOCUMENTS

| | | | |
|---|---|---|---|
| 6,327,723 B1 * | 12/2001 | Knight | 5/628 |
| 6,398,747 B1 * | 6/2002 | Rudy et al. | 602/18 |
| 6,913,584 B2 * | 7/2005 | Rudy et al. | 602/18 |
| 2002/0156409 A1 * | 10/2002 | Lee et al. | 602/18 |
| 2003/0195444 A1 * | 10/2003 | Gerstmar | 602/18 |
| 2006/0081263 A1 * | 4/2006 | Ostrowski | 128/870 |

* cited by examiner

CERVICAL IMMOBILIZING DEVICE

This application is a continuation-in-part of U.S. application Ser. No. 10/151,844 filed on May 22, 2002, now U.S. Pat. No. 6,913,584 which was a continuation application of U.S. application Ser. No. 09/427,749, filed on Oct. 27, 1999, now U.S. Pat. No. 6,398,747, for which the benefit under Title 35, U.S. Code, § 120, has been claimed.

FIELD OF THE INVENTION

The present invention relates generally to a head and cervical immobilization device. More particularly, the invention is directed to a cervical immobilization device that can be erected symmetrically to minimize movement of the head of an injured patient.

BACKGROUND OF THE INVENTION

During the transport of patients or accident victims that have suffered cervical injuries, it is essential to immobilize the head and cervical portions to prevent further injury. A variety of head and cervical immobilization devices have been used in the emergency medical industry for many years. Several of these devices are designed to fold flat during storage and can be erected when needed.

One type of head immobilizing device is designed to be attached to a rigid backboard. Other devices include a rigid structural portion that do not require the use of a rigid backboard. Examples of this type of device are disclosed generally in U.S. Pat. No. 4,034,748 to Winner, U.S. Pat. No. 4,211,218 to Kendrick and U.S. Pat. No. 4,594,999 to Nesbit.

Another type of device is disclosed in U.S. Pat. No. 4,928,711 to Williams. This device is intended to be attached to a rigid backboard for immobilizing the head of an injured patient. The device includes flexible members that are bent independently to wrap around the sides of the head and secure to the base for locking the position of the members. The head supporting members are attached to the base by a hook and pile type fastening device.

Another form of cervical immobilization device is disclosed in U.S. Pat. No. 4,964,418 to Wilson. This device has a pair of collapsible members for conforming to the patient's head. Rigid support members are then attached to a base by a hook and loop fastener for restraining the patient's head and neck.

The above-noted devices can be effective in immobilizing a patient's head and neck during transport of an injured patient. However, these devices have certain limitations and there is a continuing need in the industry for improved head immobilizing devices.

SUMMARY OF THE INVENTION

The present invention is directed to a cervical immobilization device. More particularly, the invention is directed to a collapsible cervical immobilization device that is folded to an upright position to engage the sides of a patient's head symmetrically during use.

Accordingly, a primary object of the invention is to provide a cervical immobilization device that is compact during storage and can be erected to a supporting position when needed.

Another object of the invention is to provide a cervical immobilization device that can be manufactured economically using inexpensive and readily available materials.

A further object of the invention is to provide a head immobilization device for attaching to a rigid backboard which can be folded to conform to a patient's head that is efficient and easy to use.

Another object of the invention is to provide a cervical immobilizing device that can be made from a folded blank.

Still another object of the invention is to provide a cervical immobilization device having an actuator member that enables head engaging arms to simultaneously and symmetrically engage a patient's head when folded to an operating position to eliminate or reduce movement of the patient's head.

Another object of the invention is to provide a cervical immobilization device having an actuator device that can be operated by the user with one hand to symmetrically engage both sides of the patients head to prevent twisting of the head and to support the patient's head during transport of the patient.

The objects and advantages of the invention are basically attained by providing a cervical immobilization device comprising a base having first and second ends, a first edge and a rear edge, and a cervical immobilizing member coupled to the base. The cervical immobilizing member is movable from a first position to a second upright position for engaging a patient's head. The immobilizing member has a center portion attached to the base and a pair of movable arms for engaging the patient's head when in the second upright position. Each of the arms have an inner edge coupled to the center portion by a pivotal coupling and an outer edge facing outwardly toward the respective end of the base. An actuating device is coupled to each of the outer ends of the immobilizing member. The actuating member is able to simultaneously slide the outer ends of the cervical immobilizing member from the first position toward the center portion to the upright position for supporting the patient's head. In embodiments of the invention, the center portion is a flat panel attached to the base and the arms are coupled to the center panel by fold lines.

The objects of the invention are further attained by providing a cervical immobilizing device comprising a base having a first and a second end, a front edge and a rear edge. The base has a first slot extending from the first end toward the center portion of the base and a second slot extending from the second end toward the center portion of the base. A cervical immobilizing member having a center panel is attached to the center portion of the base. The immobilizing member includes a first arm having an inner end coupled to the first edge of the center panel and an outer end spaced from the inner end. A second arm having an inner end is coupled to a second side of the center panel and has an outer end spaced from the inner end. Each of the arms include a coupling member for sliding engagement with a respective slot. An actuating device is coupled to the first and second arms for simultaneously and symmetrically sliding the outer ends of the first and second arms inwardly toward the center panel to fold each of the arms to a substantially V-shaped configuration for engaging and supporting a patient's head.

The objects of the invention are also attained by providing a blank for forming a cervical immobilizing device where the blank comprises a first panel having first and second longitudinal ends and a center panel having longitudinal ends. A first flap is coupled to the first end of the center panel by a first fold line and has a second fold line substantially parallel to the first fold line and spaced from the fold line to define an inner and an outer panel. A second flap is coupled to the second end of the center panel by a first fold line. The second panel has a second fold line parallel to and spaced from the first line to define an inner and outer panel. In certain embodiments of the invention, a first tab is coupled to the outer panel of the first flap and a second tab is coupled to the outer panel of the second flap. A connecting panel is coupled to a longitudinal side of the center panel by a fold line. A second panel having longitudinal ends and first and second longitudinal side edges is coupled to the connecting panel by a fold line along the first longitudinal side edge. The second panel has at least one first aperture adjacent the first flap and at least one second aperture adjacent the second flap.

These and other objects of the invention will become apparent to one of ordinary skill in the art in view of the following detailed description in combination with the annexed drawings, which form a part of this original disclosure.

BRIEF DESCRIPTION OF THE DRAWINGS

The following is a brief description of the drawings, in which.

DETAILED DESCRIPTION OF THE INVENTION

The present invention is directed to a cervical immobilizing device that can be folded from a generally flat position during storage to a folded upright position for engaging the sides of the head of a patient. The head immobilizing device of the invention is suitable for use in combination with a rigid backboard and is generally attached to the rigid backboard by an adhesive.

The invention is primarily directed to a foldable cervical immobilizing device that includes an actuator that is pushed or pulled by a user to fold two head-engaging arms from a collapsed, generally flat position to an upright, head engaging position to support each side of the patient's head. The actuator is able to fold the arms in a substantially symmetrical fashion to the upright position to reduce or eliminate twisting of the head and to uniformly support each side of the head. By providing the actuator, which is coupled to each of the head-engaging arms, each of the arms can be folded at the same time, thereby applying a uniform pressure in opposite directions on each side of the head and prevent twisting of the neck or lateral movement of the head that could otherwise occur if the arms were folded one at a time. The device can be made from various materials having sufficient strength to support the head of a patient. In the embodiments illustrated, the device is made of a suitable cardboard material. In further embodiments, the device can be made from plastic materials by injection molding, thermoforming or rotations molding techniques.

Figure 1:
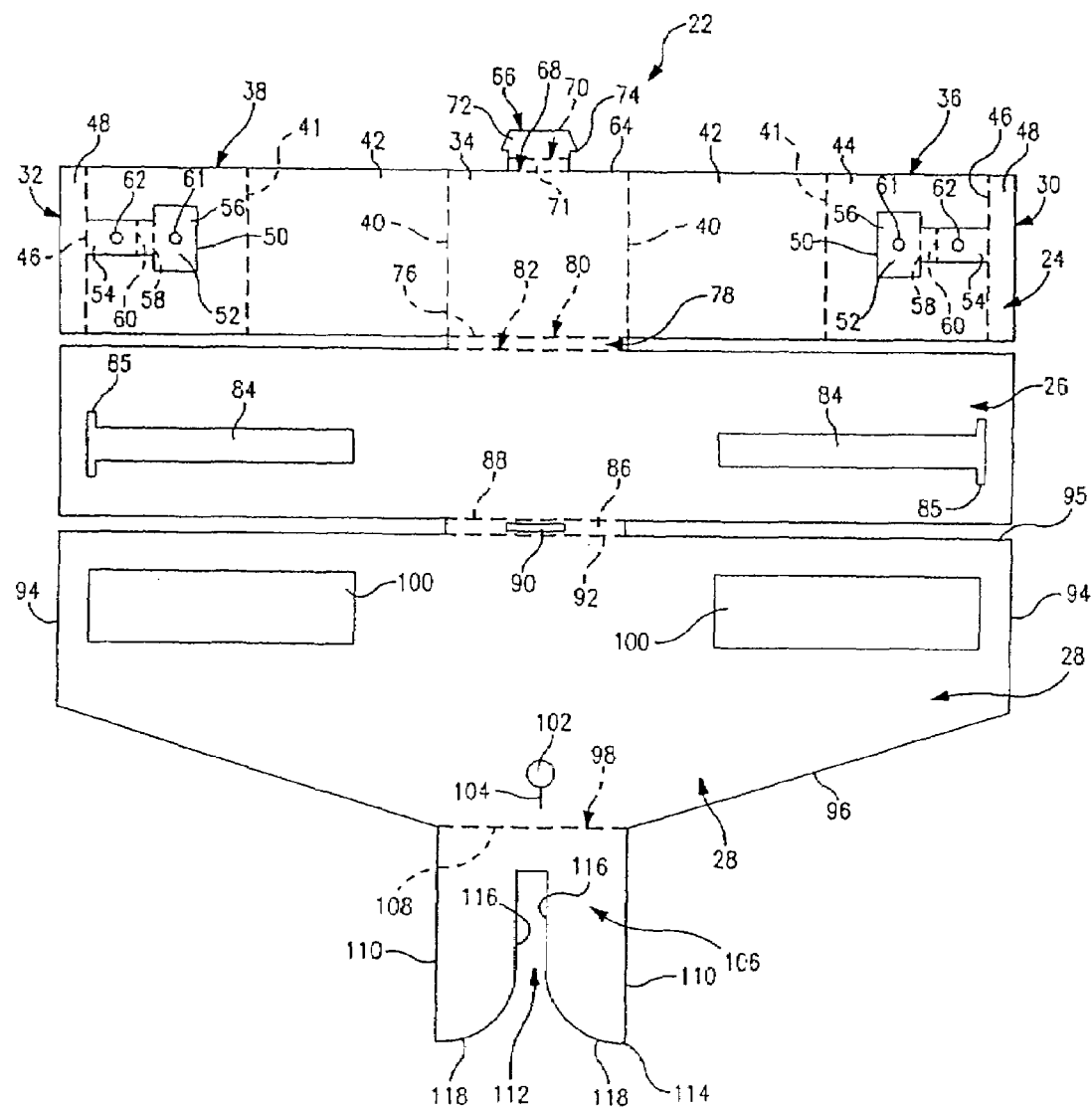
FIG. 1 is a top plan view of a blank for forming the cervical immobilizing device in a first embodiment of the invention.
Figure 2:
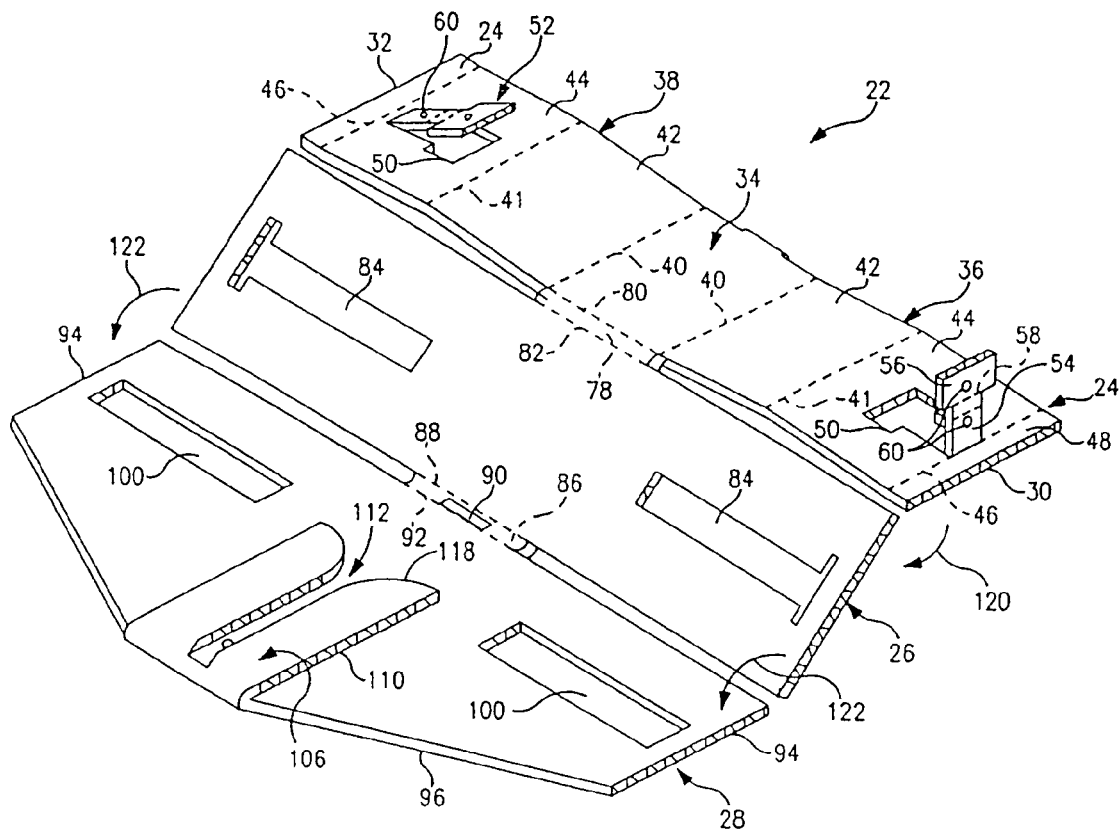
FIG. 2 is a perspective view of the blank of FIG. 1 in a partially folded position.
Figure 3:
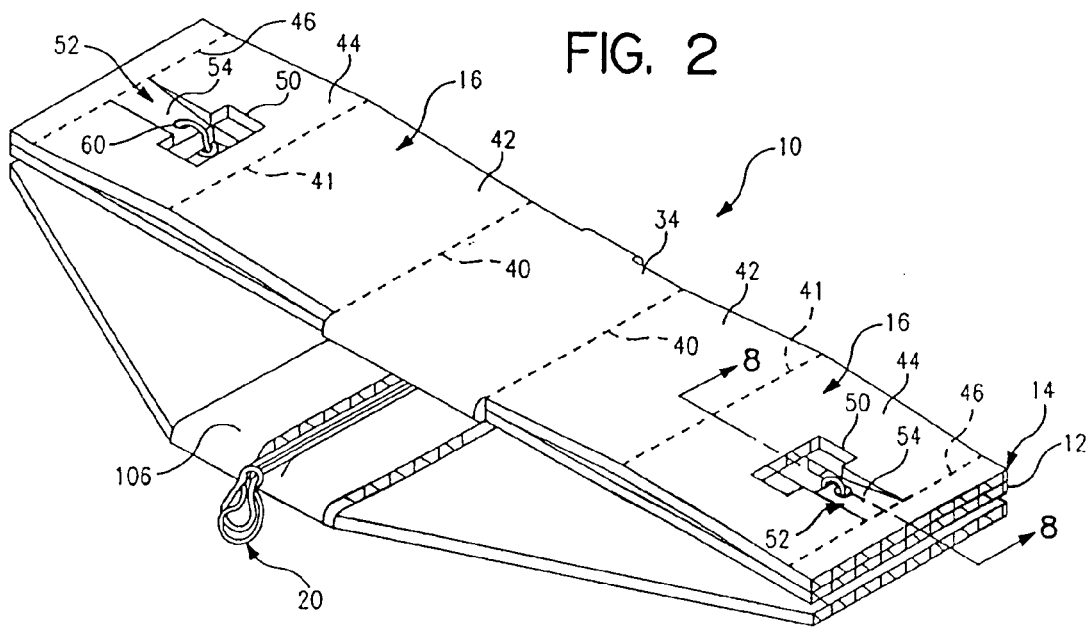
FIG. 3 is a perspective view of the cervical immobilization device formed from the blank of FIG. 1.
Figure 4:
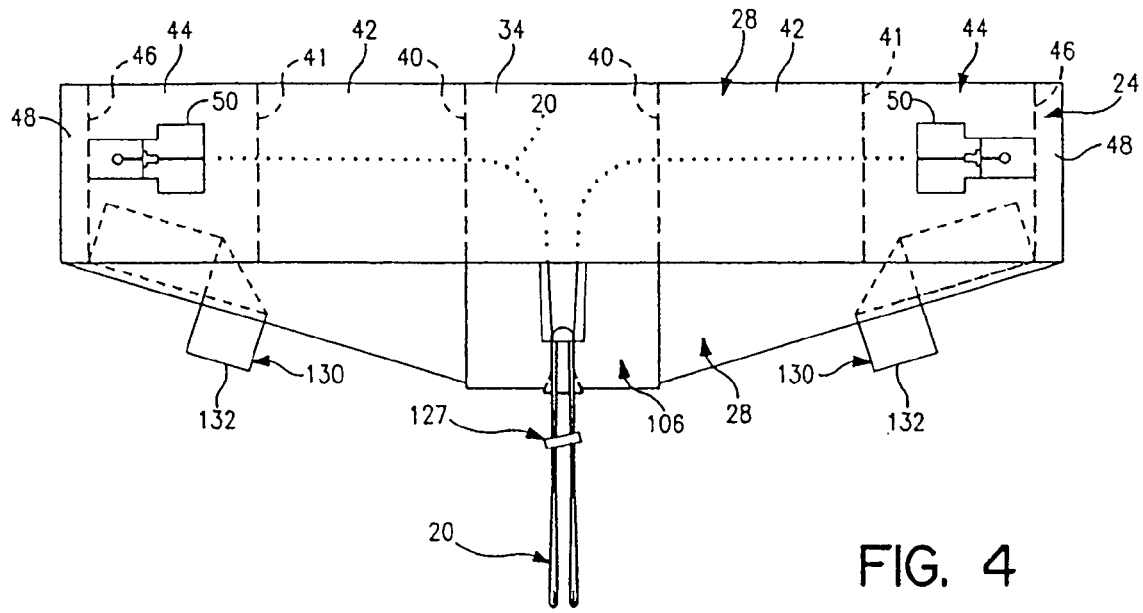
FIG. 4 is a top view of the cervical immobilization device formed from the blank of FIG. 1.
Figure 5:
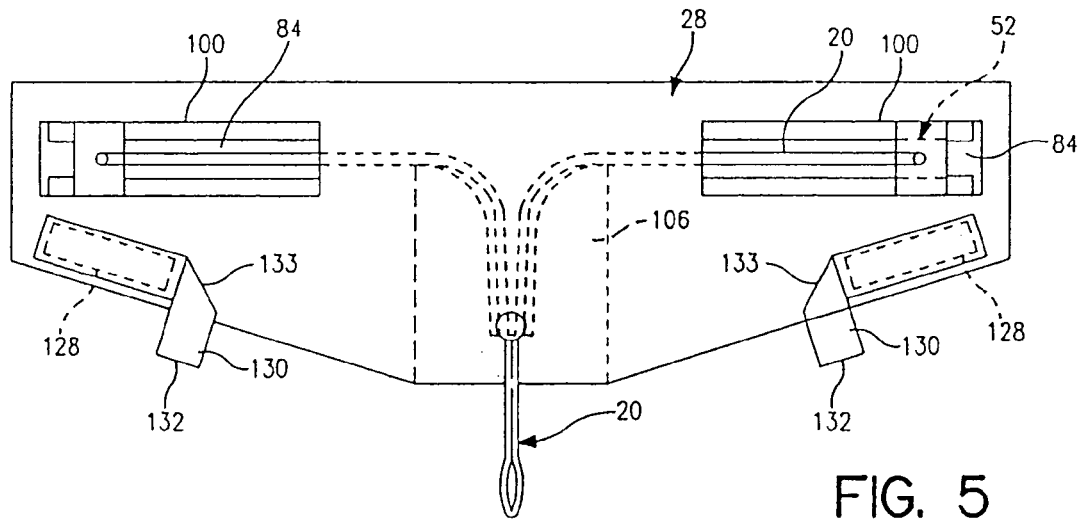
FIG. 5 is a bottom view of the cervical immobilization device formed from the blank of FIG. 1.
Figure 6:
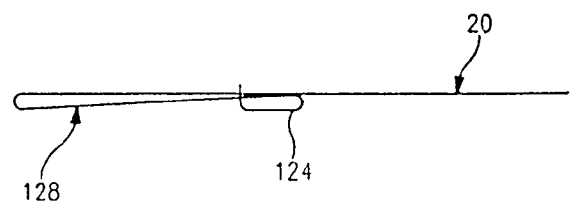
FIG. 6 is a schematic side view of the actuating device and locking arrangement of the cervical immobilization device of the embodiment of FIGS. 1–5.
Figure 7:
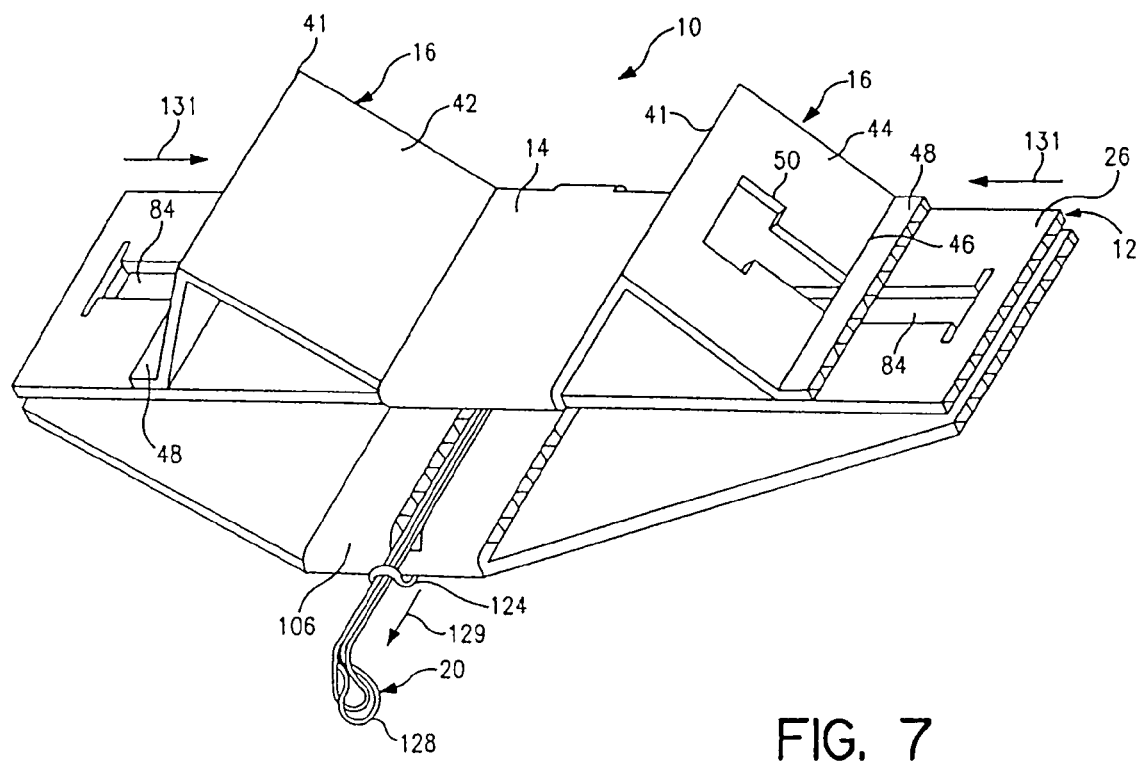
FIG. 7 is a perspective view of the cervical immobilization device in a partially erected position.
Figure 8:
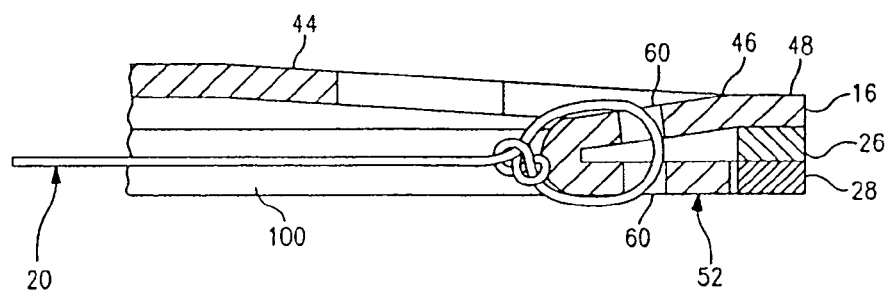
FIG. 8 is a partial cross-sectional view of the actuating member and sliding arrangement for the foldable arms as seen along line 8—8 of FIG. 3.

Referring to FIGS. 1–8, a first embodiment of the assembled cervical immobilizing device 10 and blank 22 are shown. As shown in FIGS. 3–5, the device 10 includes a first base panel 12 and a top panel 14. The top panel 14 includes two opposing arms 16 that can be folded from a flat position as shown in FIG. 3 to a folded upright position as shown in FIG. 7. An actuating device 20 is attached to each of the arms 16 so that the arms 16 can be folded to an upright position substantially simultaneously and symmetrically. Folding the arms 16 symmetrically enables the arms to simultaneously engage the two sides of the patient's head to minimize movement of the head and spine while attempting to stabilize an injured patient. In further embodiments, the actuator device is able to move the arms to an upright position one at a time. For this purpose, two actuator devices can be used.

The cervical immobilizing device 10 of the invention is generally made from a suitable sheet material having sufficient strength to support a patient's head and that can be folded along fold lines or score lines to allow for simple construction. In embodiments of the invention, the head immobilizing device is made of corrugated cardboard, although other inexpensive sheet materials, such as plastic, can be used. In further embodiments, the device can be made from separate components that are coupled together.

In embodiments of the invention, the cervical immobilizing device 10 is made from the unitary cut blank 22 as shown in FIG. 1. In the embodiment of FIG. 1, the blank 22 includes a first panel 24 that forms the top panel 14 of the assembled device 10, a second panel 26 that forms the base 12 of the device 10 and a third panel 28. The first panel 24 has a substantially rectangular shape with outer ends 30 and 32. The first panel 24 is defined by a center panel 34 and first and second flaps 36 and 38. The first flap 36 is coupled to a side edge of the center panel 34 by a fold line 40. The first flap 36 includes an intermediate fold line 41 extending parallel to the first fold line 40 to divide the flap 36 into an inner panel 42 and an outer panel 44. A fold line 46 spaced from the end 30 of the first flap 36 forms an end portion 48.

The outer panel 44 includes cut lines 50 to define a tab 52. The tab 52 includes a neck portion 54 coupled to the outer panel 44 along the fold line 46. A head portion 56 is coupled to the neck portion 54 by a fold line 58. A second fold line 60 spaced from the fold line 58 is also provided on the neck portion 54 for folding the head portion with respect to the neck portion 54 as discussed hereinafter in greater detail. In preferred embodiments, the head portion 56 has a width greater than the width of the neck portion 54. An aperture 61 is provided in the head portion 56 and an aperture 62 is provided in the neck portion 54 as shown. The second flap 38 is substantially the same as the first flap 36 so that identical elements are identified by the same reference number for simplicity.

The center panel 34 has a first side edge 64 with a coupling tab 66 coupled to the center panel along a fold line 68. A second fold line 70 defines an intermediate portion 71 and a head portion 72. The head portion 72 includes end notches 74 for engaging a slot.

The center panel 34 includes a second edge 76 attached to a coupling panel 78 along a fold line 80. In the embodiment illustrated, the coupling panel 78 has a length substantially equal to the length of the center panel 34. The second panel 26 is coupled to the coupling panel 78 along a fold line 82.

The second panel 26 has a length a width substantially equal to the length and width of the first panel and includes two substantially T-shaped slots 84. Each slot 84 has a longitudinal dimension extending parallel to a longitudinal dimension of the second panel 26. The slot 84 has a width at least equal to the width of the neck portion 54 of the tab 52 and less than the width of the head portion 56. At the outermost end of the slot 84, leg portions 85 defining the T-shape are provided to define a width at least equal to the width of the head portion 56. In a further embodiment, a single slot can be formed having a length to accommodate each of the tabs 52.

A second connecting panel 86 is coupled to the second panel 26 by a fold line 88 and is positioned opposite the coupling panel 78. Connecting panel 86 includes a longitudinal slot 90 dimensioned to receive the coupling tab 66 when the blank 22 is folded to form the immobilizing device 10. The third panel 28 is coupled to the connecting panel 86 along a fold line 92.

The third panel 28 has a longitudinal dimension substantially equal to the longitudinal dimension of the first and second panels. Side edges 94 of the third panel 28 extend perpendicular to a rear edge 95 and have a dimension substantially equal to the width of the second panel 26. In the embodiment illustrated, front edges 96 are angled with respect to the side edges 94 to converge at a leading edge 98. Two longitudinal slots 100 are cut in the third panel 28 and have a length substantially equal to the slots 84. The slots 100 have a width at least as wide as the width of the head 56 of tab 52 so that the head 56 can slide freely along the length of the slot 100. Alternatively, a single slot can be formed to receive the head 56 of each tab 52. An aperture 102 is cut in the third panel 28 proximate the leading edge 98. A slit 104 extends from the aperture 102 toward the leading edge 98.

As shown in FIG. 1, an end panel 106 is coupled to the leading edge 98 of the third panel 28 along a fold line 108. The end panel 106 has a width substantially equal to the length of the leading edge 98 and parallel sides 110 extending perpendicular to the edge 98. An elongated slot 112 extends from an outer end 114 parallel to the sides 110 and is generally aligned with the aperture 102. The slot 112 includes side edges 116 that are substantially straight and terminate in a curved, convex portion 118.

As shown in FIG. 2, the immobilizing device 10 is assembled by folding the first panel 24 along fold lines 80 and 82 onto the second panel 26 in the direction of arrow 120 and the tab 66 is inserted into the slot 90. The second panel 26 is folded along fold lines 88 and 92 onto the third panel 28 in the direction of arrow 122. The end panel 106 is folded along fold line 108 onto the third panel 28 and secured in place by a suitable adhesive or fastener. The second panel 26 is secured to the panel 106 by an adhesive. For purposes of illustration, the tabs 52 are shown folded upwardly from the plane of the first panel 24. During assembly of the immobilizing device 10, the tabs 52 are folded downwardly and inserted through the slots 84 so that the head portion 56 is on the opposite side of the second panel 26 from the first panel 24. The slots 84 and 100 are superimposed so that the head 56 of tab 52 is able to slide.

As shown in FIG. 3, the assembled immobilizing device 10 includes the base 12 formed by the second panel 26 and a top panel 14 formed by the first panel 24. The flaps 36 and 38 of the blank 22 form the folding arms 16. The tab 52 is folded along the fold lines 58 and 60 so that the tab 52 couples the arms 16 to the base 12 in a sliding manner. In this embodiment, the actuating member 20 is a flexible cord or string. Each end of the cord passes through the apertures 60 and 61 of a respective tab 52. The end panel 106 forms a guide on the third panel 28 for the cord 20. As shown in FIG. 4, the cord passes between the arms 16 and the base 12 and around the convex portions 118 of panel 106 and along the open slot 112. As shown schematically in FIG. 6, the end of the cord 20 passes downwardly through the aperture 102 in the third panel 28 to form a loop 124. The remaining portion of the cord 20 that is not passed through the aperture 102 is pulled through the loop 124 to form a second loop 126. A fastener 127 can be attached to the cord to secure the two sections of the cord together.

The immobilizing device 10 is generally intended to be used in combination with a rigid backboard (not shown). For this purpose, a double-faced adhesive strip 128 is provided on the bottom face of the third panel 28 along each edge as shown in FIGS. 4 and 5. A release layer 130 having a tab 132 extending outwardly from the top edge of the device covers the adhesive strip 128. The immobilizing device 10 is positioned on a rigid board or other substrate and the release layer 130 is pulled to separate the release layer from the adhesive strip and expose the adhesive, whereby the device can be attached to the board.

In a preferred embodiment, the release layer 130 has a length longer than the length of the adhesive strip 128. The tab 132 is folded along a fold line 133, generally at about a 45° angle, to extend perpendicular to the longitudinal dimension of the adhesive strip. The release sheet is removed by pulling in a direction generally perpendicular to the adhesive strip, which peels the release layer from the adhesive.

In use, the immobilizing device is placed under the head of a patient with the center panel 34 positioned directly below the patient's head. The center panel 34 is generally dimensioned to accommodate the head of a patient. The actuating device 20 is pulled in the direction of arrow 129 of FIG. 7 to apply a tension to the ends of the cord coupled to the tabs 52. Pulling on the actuating device 20 in a preferred embodiment applies a simultaneous and symmetrical force to the tabs 52 which pulls the outer ends of the arms 16 inwardly toward the center panel 32 in the direction of arrows 131. As the outer ends of the arms 16 are drawn toward the center panel 34, the arms 16 fold along the fold lines 40 and 46, whereby the arms 16 assume a folded, upright, substantially inverted V-shaped configuration as shown in FIG. 7. The inner panels 42 preferably simultaneously contact the opposite sides of the patient's head with substantially uniform pressure and tension to eliminate or reduce movement of the patient's head during the folding of the arms 16. Alternatively, the actuating device 20 can be arranged to apply a non-uniform force against each side of the patient's head as needed and to separately move the arms from the flat position to the folded upright position. For example, the length of cord attached to each tab can be pulled separately to separately raise each arm to the folded position. In still further embodiments, two separate actuator devices can be included to selectively move the arms to the upright position at a desired time.

Once the arms 16 are folded to the desired upright position, the position of the arms is locked by pulling on the cord 20 to tighten the first loop 124 around the cord and to pull the cord 20 into the slit 104. The slit 104 is sufficiently thin to frictionally grip the cord 20. The loop arrangement of the cord 20 enables the cord to be cinched and held in a fixed position and to provide infinite adjustment of the position of the arms 16 with respect to the base 12. The inner panels 42 are preferably able to bend slightly to conform to the shape of the patient's head as the cord is pulled and support the user's head by preventing movement and preventing further injury. A plurality of fold lines (not shown) can be provided on the inner panels 42 to allow the inner panels to fold and conform to the patient's head. The patient can be removed from the device 10 by loosening the loop 124, thereby loosening the cord and allowing the arms 16 to be unfolded and moved away from the patient's head. In actual use, an adhesive backed tape or strap is generally attached to the arms 16 and passed over the forehead of the patient to secure the patient's head to the immobilizing device 10.

It will be appreciated that the cervical immobilizing device 10 can be made from a folded blank having an arrangement of panels different from the embodiment of FIG. 1. In further embodiments, the panels can be separate elements that are assembled and secured together by adhesives or other fasteners. Other locking devices can be used to lock the actuator device in a fixed position and retain the arms in the upright position. For example, a post or button-like device can be attached to the upper surface of the immobilizing device so that a cord can be wrapped around the post to secure the cord in place.

Figure 25:
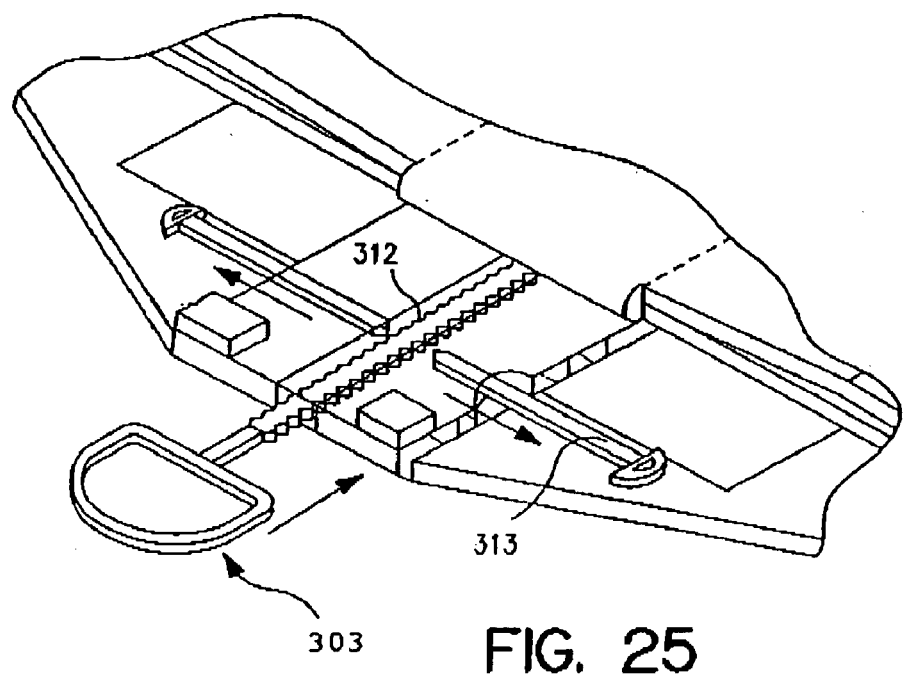
FIG. 25 is a perspective view of the invention with a lock for the actuator device.
Figure 26:
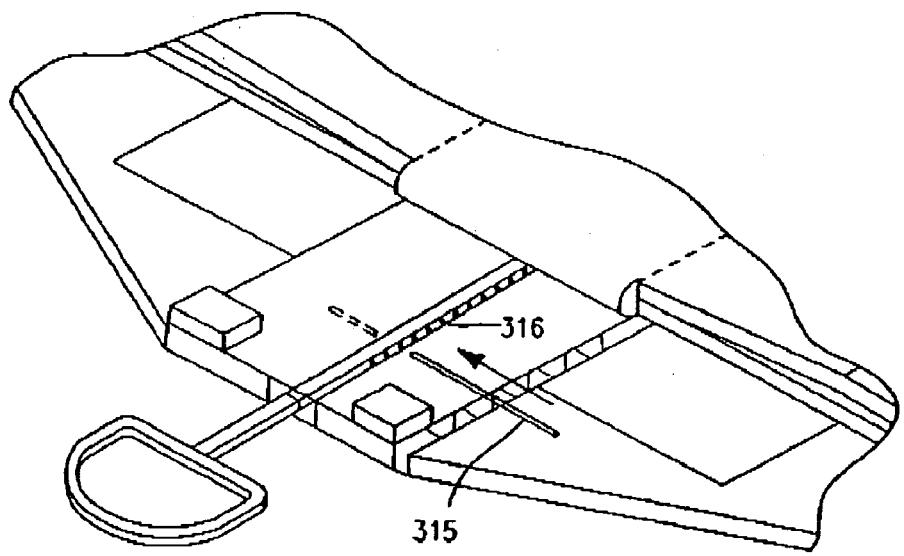
FIG. 26 is a perspective view of the invention with a lock for the actuator device.
Figure 27:
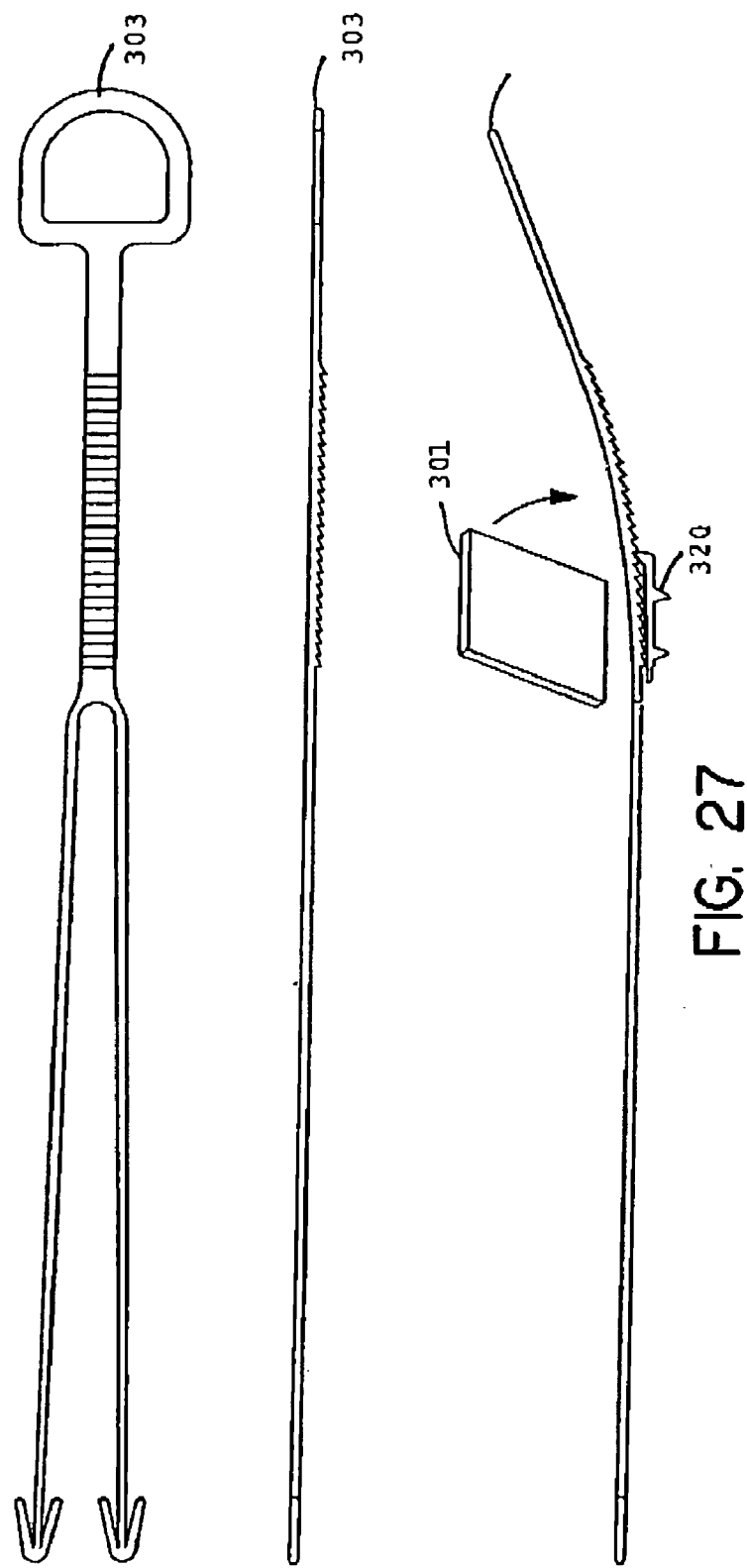
FIG. 27 presents top, side, and perspective views of an actuator device.

FIGS. 21 through 26 represent other embodiments of locking devices that can be used to lock the actuator device, such as the actuator device shown in FIG. 27, in a desired fixed position. These locking devices are examples of desirable embodiments but are not an exhaustive representation of all embodiments of locking devices for this purpose. One skilled in the art can readily derive additional structures for locking devices from the teachings of these examples. The following embodiments are desirable because these embodiments provide a reliable locking device that is quick and simple to use and does not require the emergency medical personnel using the cervical immobilization device to move the device or patient's head unnecessarily. Also, these embodiments of the locking device can be made by standard manufacturing procedures from inexpensive materials.

Desirable embodiments of the locking device for the actuator device include a member selected from the group consisting of cinching device, ratcheting device, a clamping device, and combinations thereof. Desirable embodiments of these structures can include a member selected from the group consisting of a latch, ratchet and pawl structures, pin and stopper structures, raised surfaces with complementary receiving apertures, a releasable clamp, hook and loop fabric, releasable adhesive, friction devices, and comparable means for locking an actuator device. Additionally, each of these locking devices can have multiple structures that vary from one another.

Figure 21:
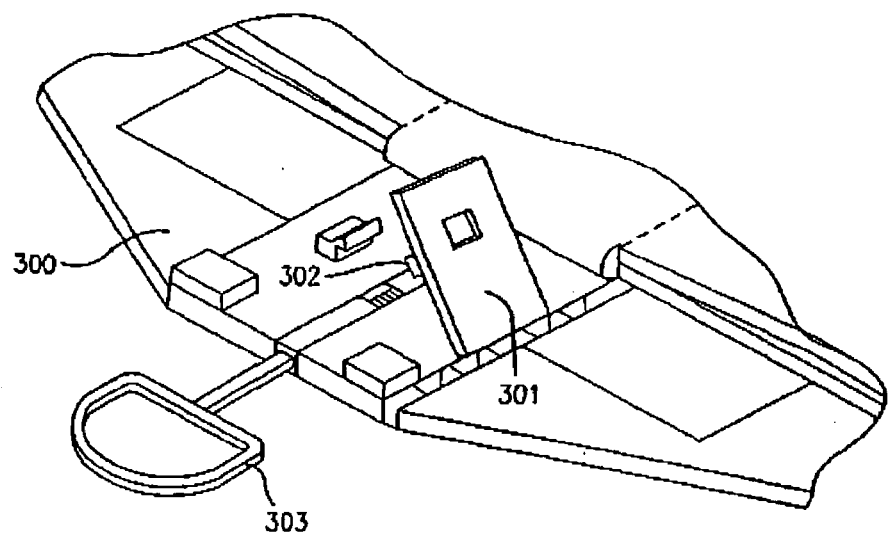
FIG. 21 is a perspective view of the invention with a lock for the actuator device.

FIG. 21 illustrates a locking device for a cervical immobilization device 300 having a latch 301 with at least one protrusion 302. A protrusion can be a tooth, a notch, a pin or comparable means for engaging an actuator device 303. The latch 301 can be on the top, bottom, and/or one or both sides of the actuator device 303. The latch can be snapped or otherwise pressed onto the cervical immobilization device 300. Compressing the latch 301 into a fixed locking position on the cervical immobilization device 300 presses the protrusion 302 into the actuator device 303. The protrusion 302 applies a friction hold or otherwise engages with at least one tooth, notch, pin, or comparable means for engaging a complementary aperture, slot, hole, groove, or receiving means in the actuator device 303. FIG. 21 is an embodiment having one tooth which engages and fits in a slot between two complementary teeth on the actuator device 303.

Figure 22:
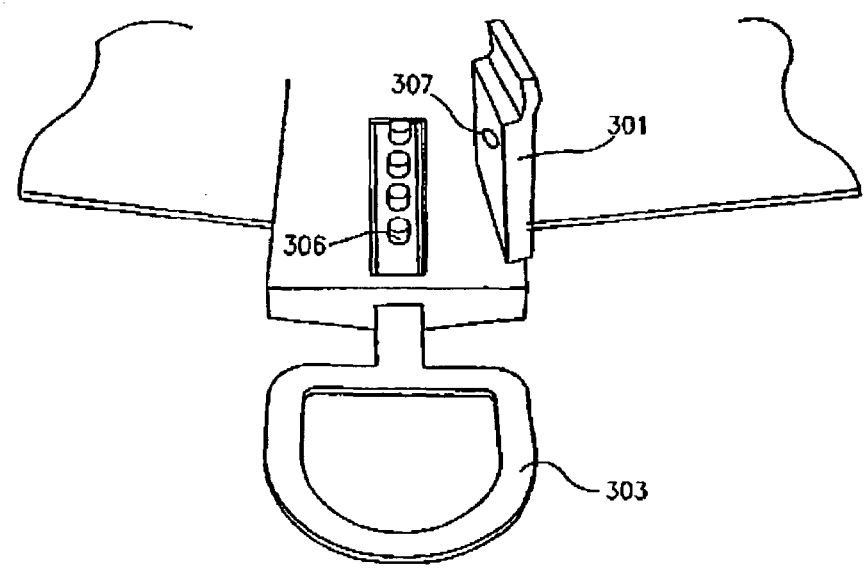
FIG. 22 is a perspective view of the invention with a lock for the actuator device.
Figure 23:
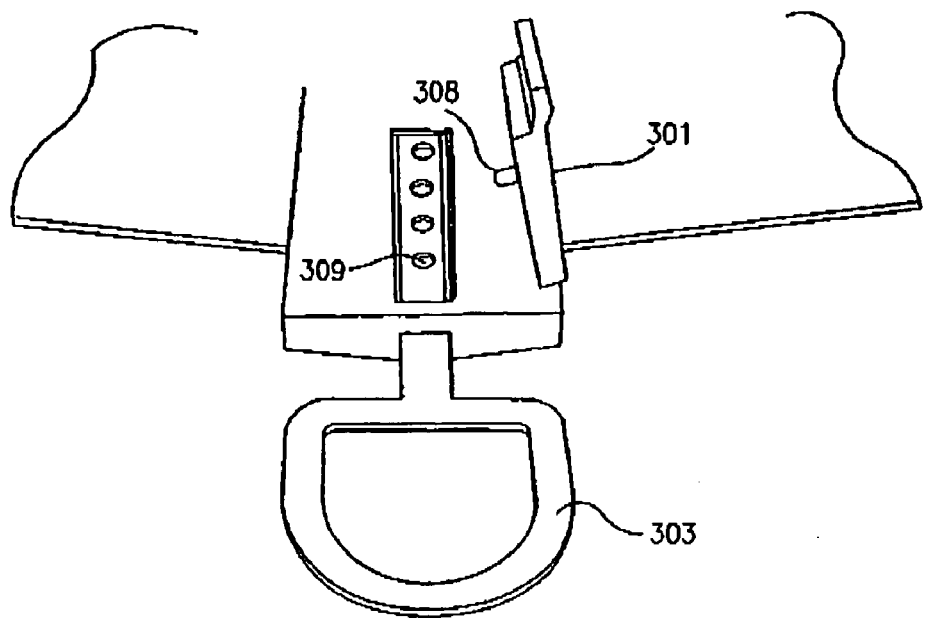
FIG. 23 is a perspective view of the invention with a lock for the actuator device.
Figure 24:
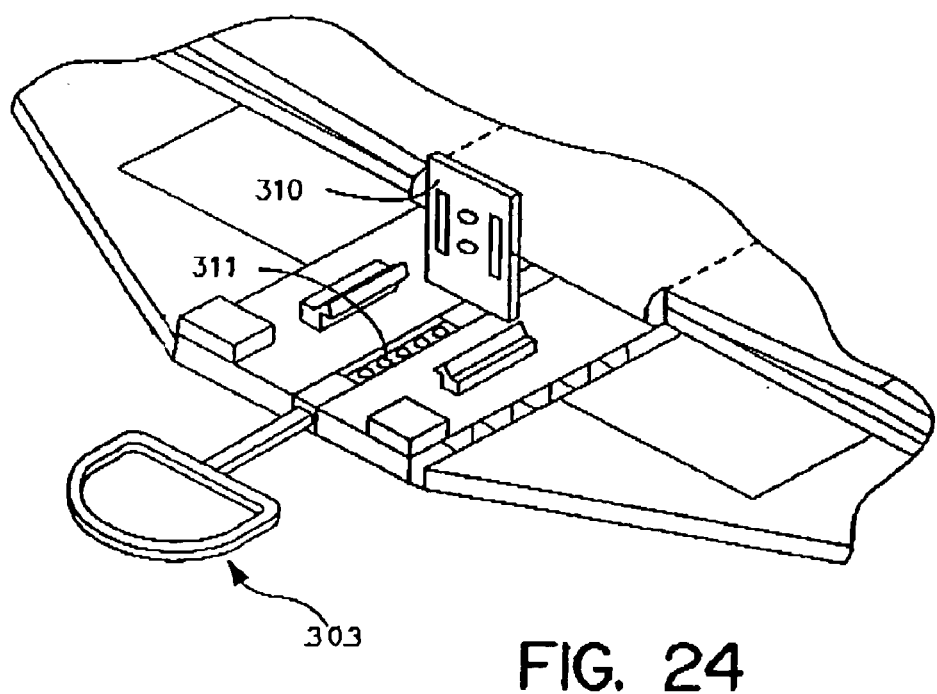
FIG. 24 is a perspective view of the invention with a lock for the actuator device.

FIG. 22 illustrates an embodiment of the locking device wherein the actuator device 303 has a plurality of raised pins 306. The pins 306 engage a stopper structure, which in this embodiment is a rack of complementary apertures 307 on the latch 301. FIG. 23 illustrates an embodiment of the locking device wherein the latch 301 has at least one tooth 308 which passes through a perforation 309 in the actuator device 303. FIG. 24 illustrates an embodiment of a locking device with its hinge transcending and mounted over the actuator device 303. The latch 310 of this embodiment has recessed apertures or dimple-like structures, which engage complementary domes or raised projections 311 on the actuator device.

FIGS. 25 and 26 illustrate embodiments of the locking device wherein pawls, pins, clamps, hook and loop fabric, releasable adhesive, or other gripping means engage the side of an actuator device. In these embodiments the pawls, pins, or gripping devices can be tension-mounted (not shown) such that the actuator device 303 is pulled into place and the ratchet and pawl, for example, automatically lock and hold the actuator device 303 in a locked position because of the tension device pushing the pawl into the ratchet. The locked position can be released when an operator releases the tension device which forces the pawl into the ratchet. The release of the tension device allows the actuator device to be pushed back into the inoperable storage position.

FIG. 25 illustrates a ratchet 312 with two opposing pawns 313 to engage the actuator device 303 between opposite ratchet teeth. The pawls can be pinched together by the operator. Alternatively, a tension device can be used to push the palws into the ratchet of the actuator device 303.

FIG. 26 illustrates an embodiment of the locking device having at least one pin 315 which slides into or through at least one complementary aperture 316 or stopper structure in the actuator device 303.

FIG. 27 presents a top, side, and perspective view of an actuator device 303. The latch 301 can be pressed on to the actuator device 303 to push the teeth or other receptacles of the actuator device 303 into the catch 320.

Figure 9:
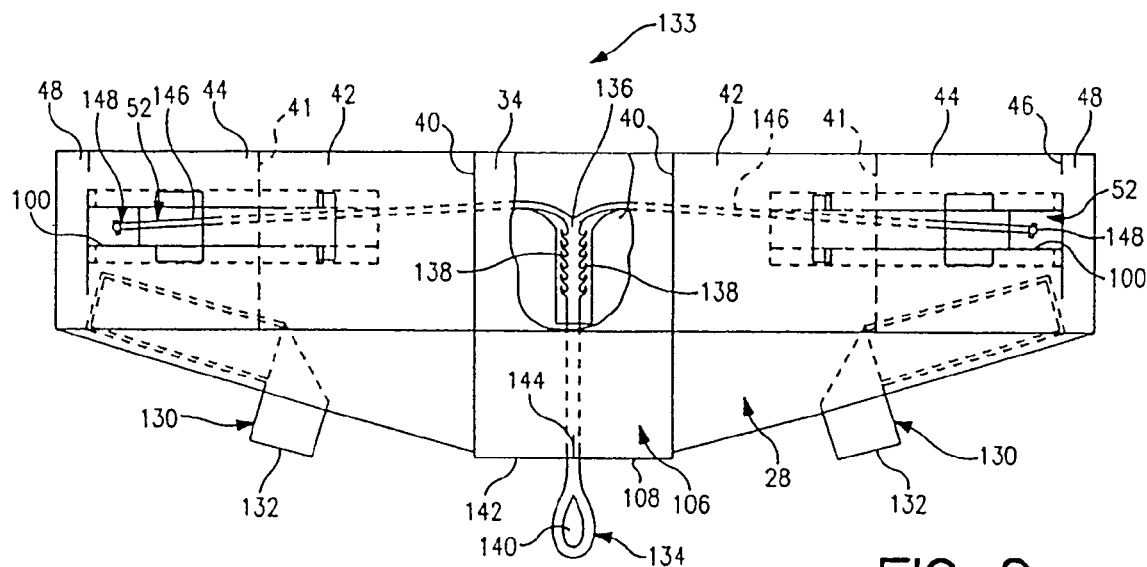
FIG. 9 is a top view of the cervical immobilization device in a second embodiment of the invention.
Figure 10:
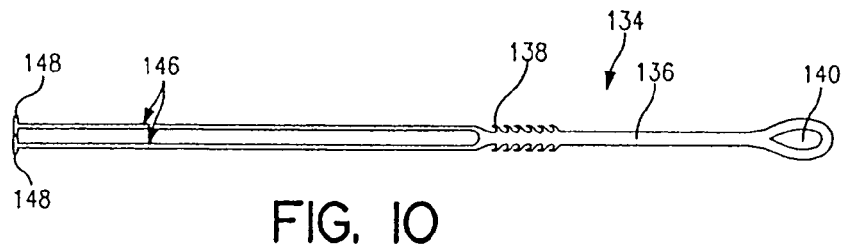
FIG. 10 is a top plan view of the actuator device for the cervical immobilization device of FIG. 9.
Figure 11:
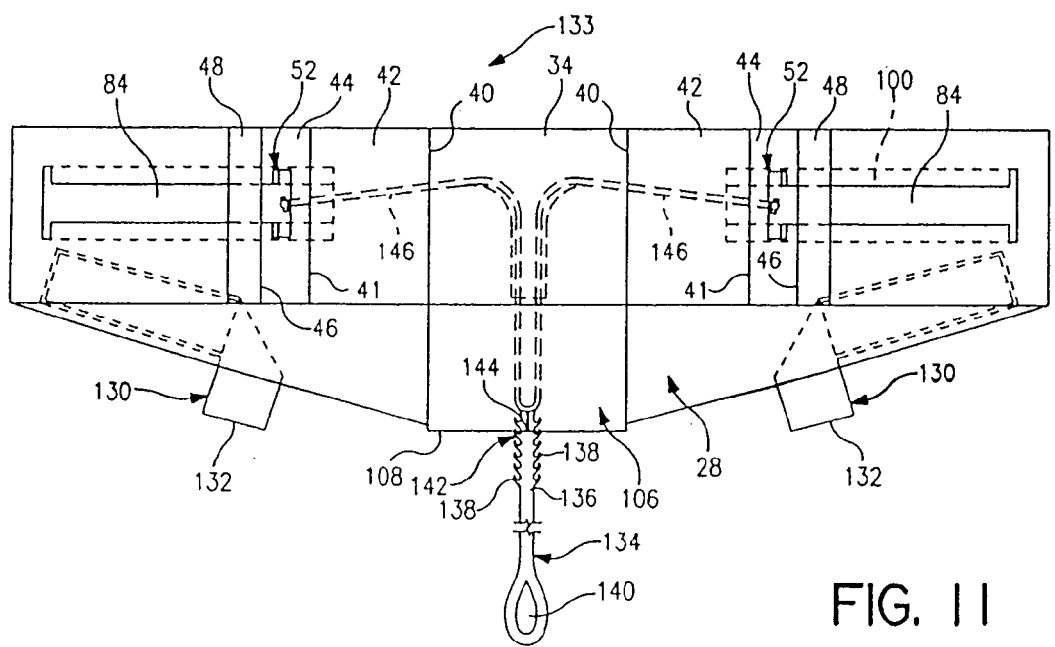
FIG. 11 is a top view of the cervical immobilization device of the embodiment of FIG. 9 showing the head supporting arms in the erected position.

A second embodiment of the cervical immobilizing device 133 of the invention is illustrated in FIGS. 9–11 and is similar to the immobilizing device 10 of the embodiment of FIG. 1 except for the actuating device 134. The cervical immobilizing device 133 of this embodiment is made from a blank substantially the same as the blank 22 of FIG. 1. Accordingly, identical components and parts of the immobilizing device 133 are identified by the same reference number. In this embodiment, the actuating device 134 includes a body portion 136 having a plurality of ratcheting teeth 138 on opposite sides of the body portion 136. A gripping end 140 is provided in the form of a loop. In this embodiment, a slit 142 is provided along the fold line 108 having a length substantially equal to the width of the body portion 136 and less than the outer dimension of the teeth 138. A transverse slit 144 is cut perpendicular to the slit 142 to allow the loop 140 to be inserted and positioned in the slit 142. In the embodiment illustrated, the transverse slit 144 is formed in panel 106 so that the slit 144 appears on the top portion of the device 133. Alternatively, the slit 144 can be formed in the panel 28 to appear on the bottom of the device 133. As shown in the cut-away view of FIG. 9 and the top view of FIG. 8, the actuating device 134 includes two flexible leg members 146 extending from the body portion 136 to the tabs 52. The flexible legs 146 include an enlarged T-shaped head 148 for passing through the apertures 61 and 62 and coupling with the tab 52.

The immobilizing device 133 of the embodiment of FIGS. 9–11 is used in a similar manner as the embodiment of FIGS. 1–8. Basically, the immobilizing device 133 is fixed to a rigid backboard and the patient's head is placed on the center panel 34 with the actuating device 134 extending away from the patient's body. The loop 140 is pulled away from the immobilizing device 133 so that the flexible legs 146 of the actuating device 134 pull the ends of the arms 16 toward the center panel 34 and fold the arms 16 along the fold lines 40 and 41 to the upright position. The actuating device 134 is pulled until the teeth 138 pass through the slit 142 so that the teeth engage the sides of the slit 142 to lock the actuating device 134 in a fixed position, thereby locking the arms 16 in a folded, upright position. As can be seen in FIG. 11, the teeth 138 form a one-way ratchet mechanism with the slit 142 for adjusting and locking the position of the arms 16.

Figure 12:
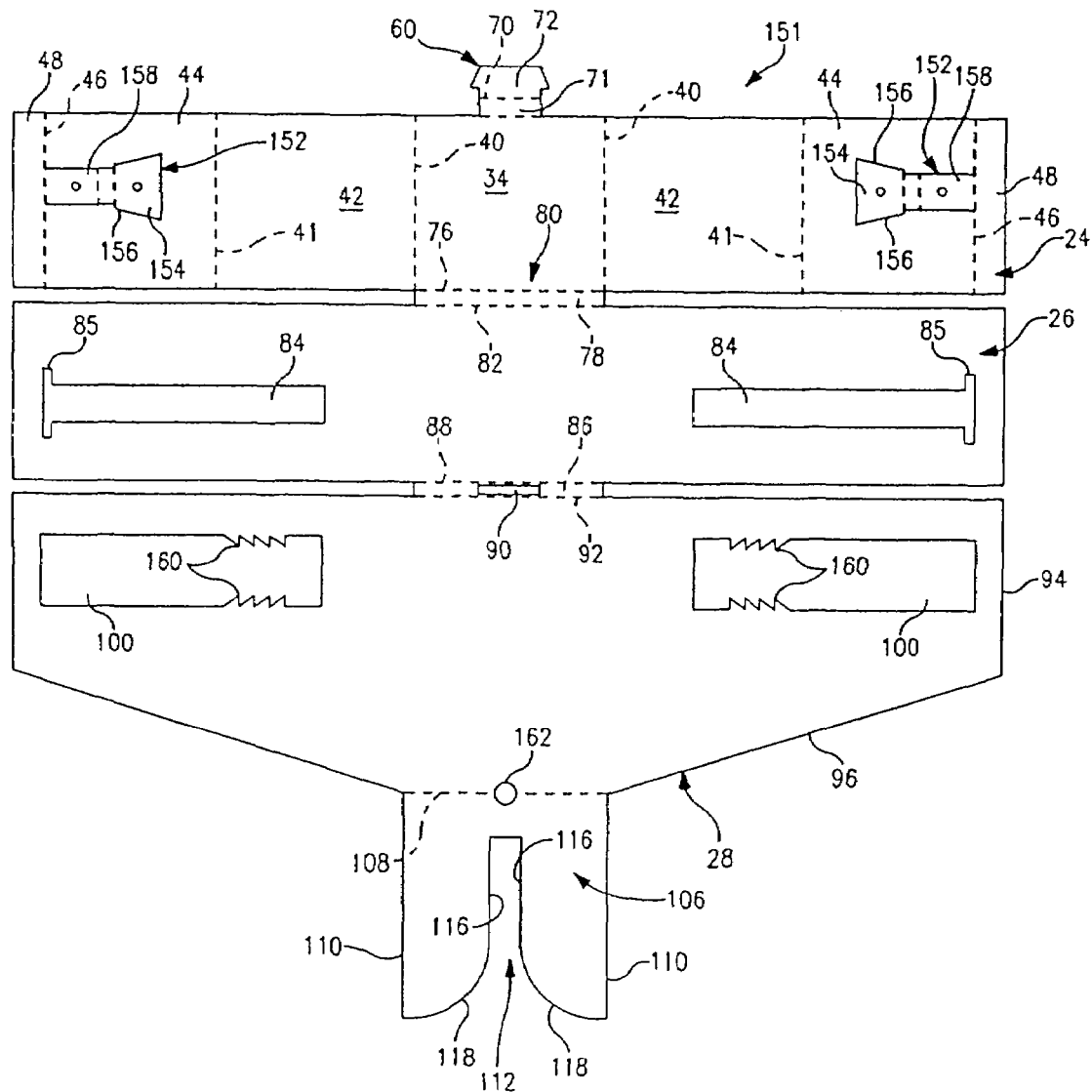
FIG. 12 is a top plan view of a blank for forming a cervical immobilization device in a third embodiment of the invention.

FIGS. 12–15 illustrate a third embodiment of the invention. In this embodiment, the immobilizing device 150 is similar to the device of FIG. 1 so that similar elements are identified by the same reference number. FIG. 12 shows a blank 151 for forming the immobilizing device 150 and includes panels 24, 26, 28 and 106 that are substantially the same as the previous embodiments. This embodiment differs primarily from the embodiment of FIG. 1 in that the outer panels 44 include a cut portion 50 to form tabs 152 having a substantially trapezoidal-shaped head 154. As shown, the head 154 includes angled sides 156 which converge toward the neck portion 158.

The slots 100 in panel 26 include a plurality of teeth 160 extending inwardly from each side of the slot. The teeth 160 are dimensioned to interlock with the angled sides 156 of the tabs 152. As shown, the teeth have a first face 161 angled in the direction of the outer edges and a second face 163 extending substantially perpendicular to the side edge of the slot 100. Alternatively, a single slot can be formed to accommodate the tabs 152. A hole 162 is punched along the fold line 108 for the actuating device 164.

Figure 13:
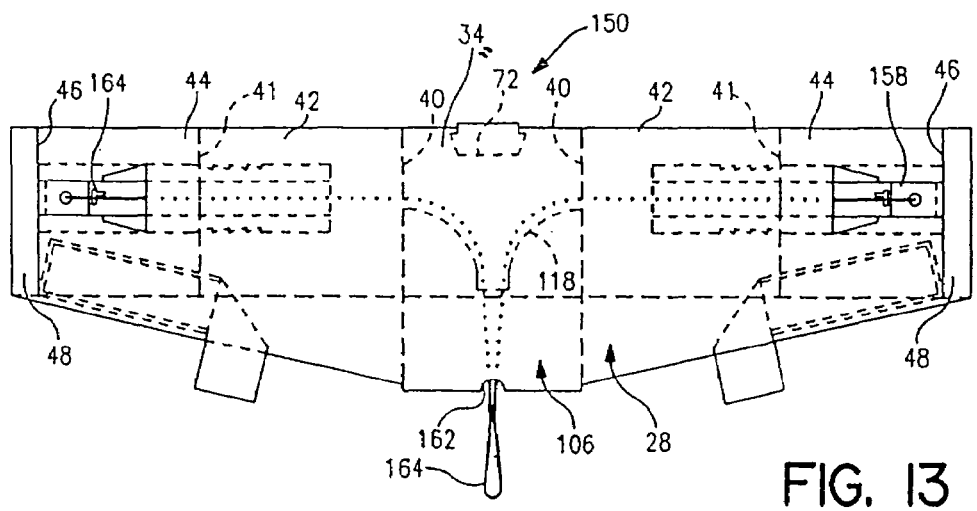
FIG. 13 is a top view of the cervical immobilization device formed from the blank of FIG. 12.
Figure 14:
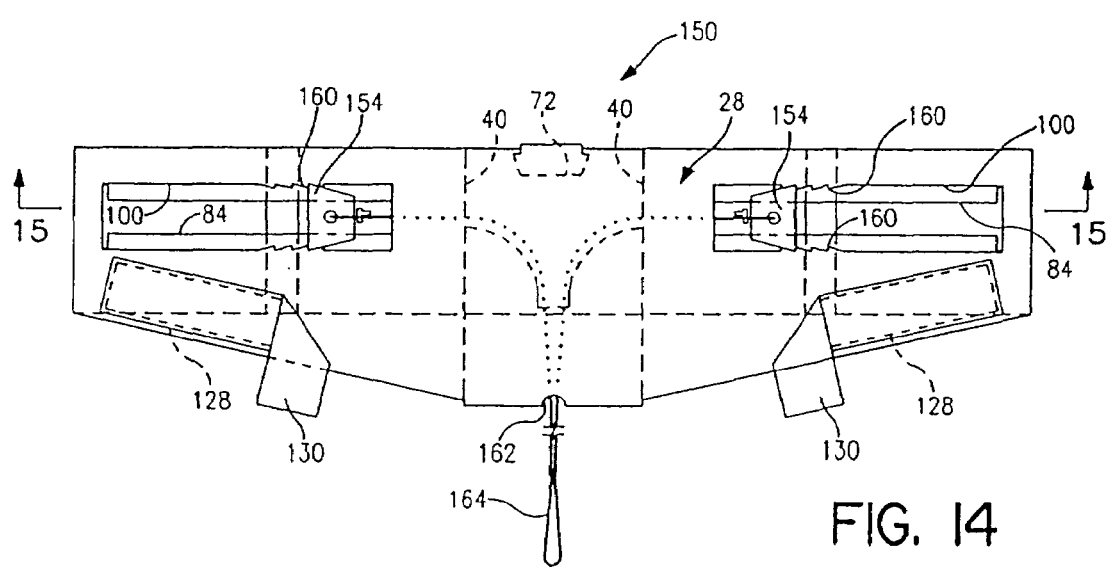
FIG. 14 is a bottom view of the cervical immobilization device of FIG. 13 showing the head engaging arms in the folded position.
Figure 15:
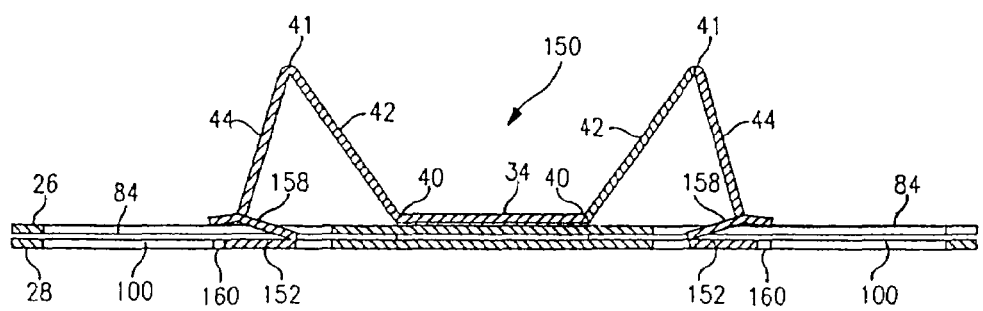
FIG. 15 is a cross-sectional view showing the head engaging arms in the folded position.

FIG. 13 is a top view of the assembled immobilization device 150. As shown, the actuating device 164 is a flexible member such as a string or cord attached to each coupling tab 152 and passes through the hole 162 around each of the convex surfaces 118. The actuating device 164 is pulled outwardly from the immobilizing device 150 which pulls the tabs 152 and the outer ends of the arms 16 toward the center panel 34 as in the previous embodiments to the upright folded position as shown in FIG. 15. As shown in FIG. 14, pulling the actuating device 164 pulls the tabs 152 along the slot 100 where the sides 156 engage the teeth 160 in a ratcheting motion. The edges 156 engage the teeth 160 to lock the tabs 152 in a fixed position. As shown in FIG. 15, the teeth 160 allow the tabs to slide or ratchet in the direction of center panel 34 and prevent the tabs 152 from sliding back to the original position. In further embodiments, the tabs 152 can be moved manually by the user by pushing inwardly on each tab until the teeth 160 engage the edges of the tab to lock the tabs in position. In this embodiment, the actuator device can be eliminated where the tabs are to be moved manually.

Figure 16:
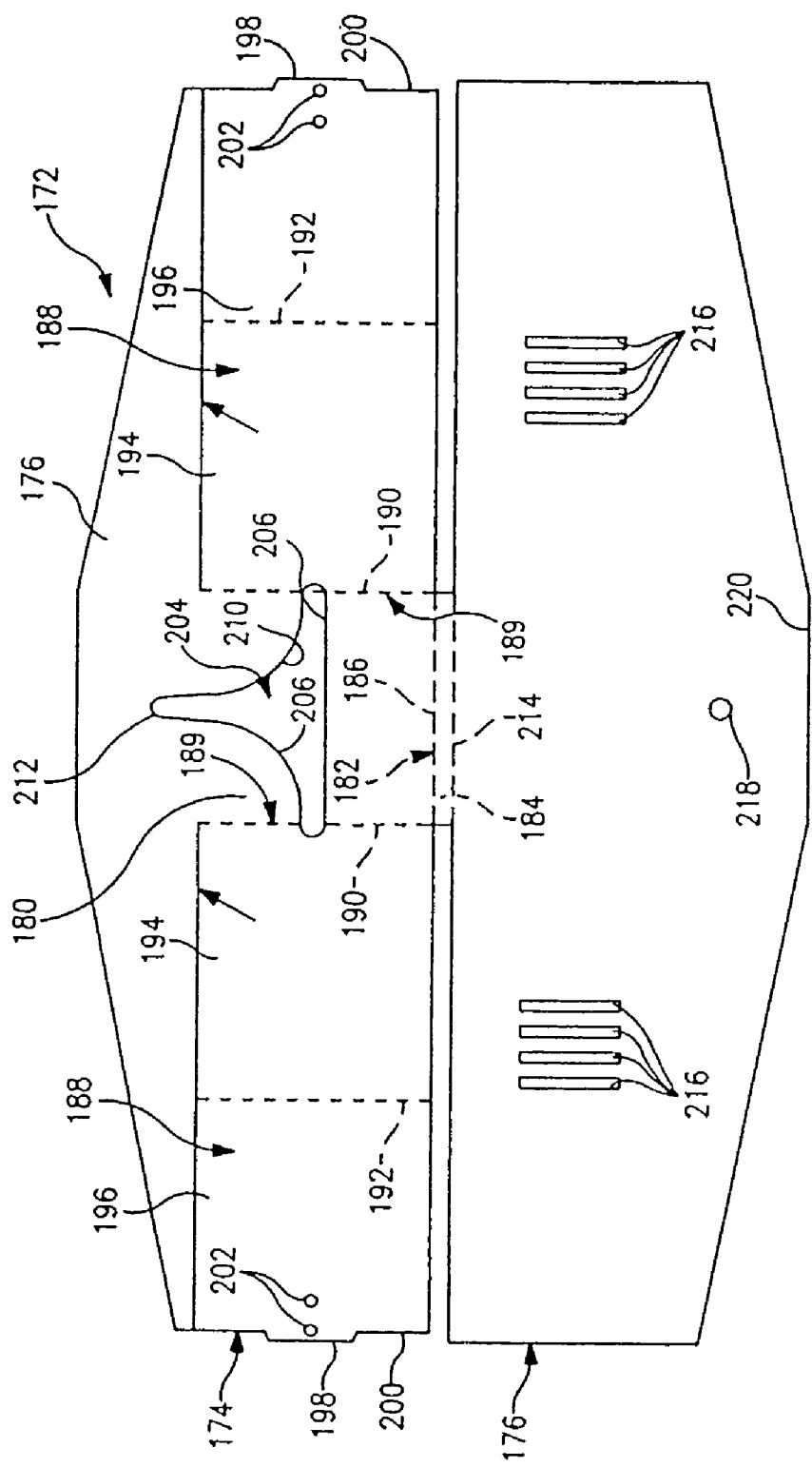
FIG. 16 is a top plan view of a blank for forming a cervical immobilization device in a further embodiment of the invention.
Figure 17:
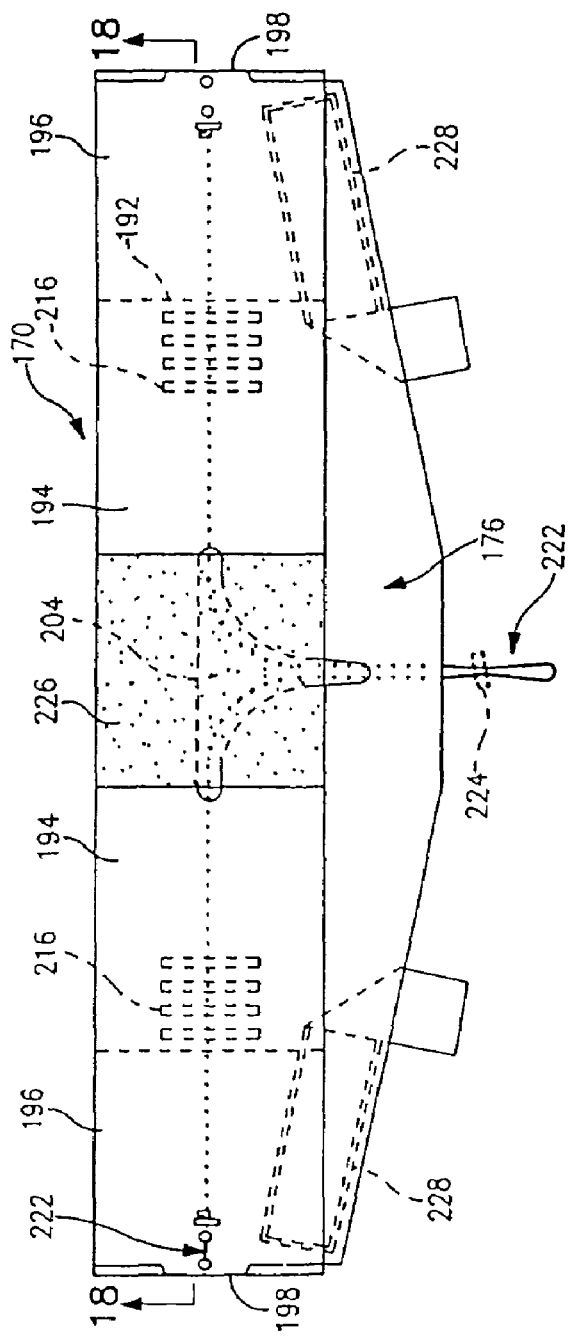
FIG. 17 is a top view of a cervical immobilization device formed from the blank of FIG. 16.
Figure 18:
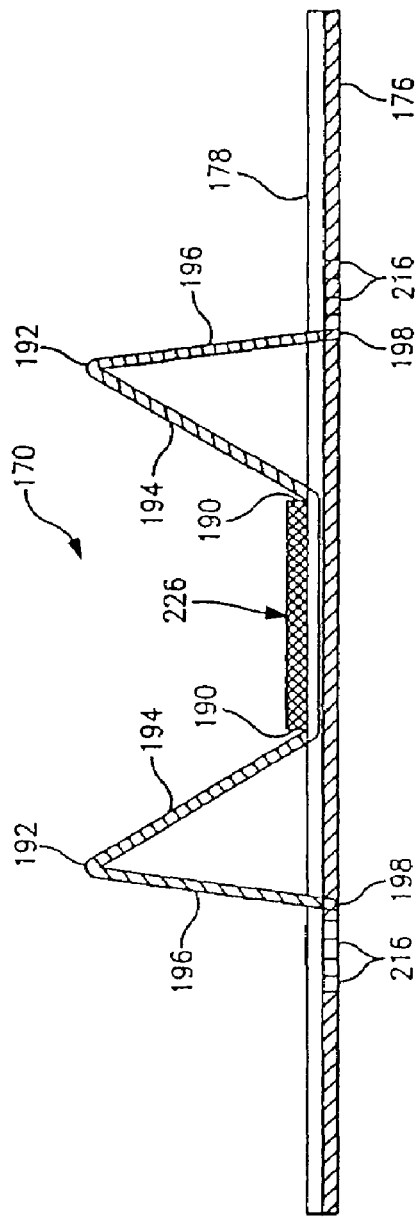
FIG. 18 is a cross-sectional view of the cervical immobilization device of FIG. 17 showing the head supporting arms in the folded position.

Referring to FIGS. 16–18, a further embodiment of the invention is illustrated. This embodiment is similar to the previous embodiments, except that the cervical immobilizing device 170 is formed from two layers of material superimposed on one another. The cervical immobilizing device 170 is formed from a blank 172 as shown in FIG. 16. The blank 170 includes a first panel 174 and a second panel 176. The first panel 174 includes an outer portion 178 extending the length of the first panel in the longitudinal direction and is integrally formed with a center panel 180. The center panel 180 has a longitudinal edge 182 coupled to a coupling panel 184 by a fold line 186. The center panel 180 also has transverse side edges 189 coupled to identical flaps 188 by fold lines 190. Each of the flaps 188 have a longitudinal dimension extending to the edge of the outer portion 178. The flaps 188 include a center fold line 192 to define an inner panel 194 and an outer panel 196. A coupling tab 198 extends from the edge 200 of the outer panel 196. A pair of apertures 202 are formed in the outer panel 196 adjacent the coupling tab 198.

The center panel 180 includes a center aperture 204 having a generally triangular shape. The aperture 204 has a first edge 206 extending in the longitudinal direction of the first panel 174 and has a length slightly greater than the width of the center panel 180 so that the aperture 204 extends into each inner panel 194. A second edge 208 and a third edge 210 extend from the first edge 206 and converge to an apex 212. The second and third edges have a generally convex shape as shown in FIG. 16. As shown, each of the side edges join an adjacent side edge at a generally curved intersection.

The coupling panel 184 is coupled to the second panel 176 by a fold line 214. The second panel 176 has an overall dimension and shape substantially the same as the first panel 174. As shown in FIG. 16, a plurality of spaced-apart slots 216 are formed in the second panel extending in a generally transverse direction with respect to the longitudinal dimension of the second panel 176. The slots 116 have a length and width sufficient for receiving the coupling tab 198. A central aperture 218 is provided in the second panel 176 proximate the outer longitudinal edge 220 of the second panel 176.

The cervical immobilizing device 170 as shown in FIG. 17 is formed by folding the first panel 176 along fold lines 186 and 214 so that the first and second panels are superimposed on one another. The outer portion 178 of the first panel 174 and the center panel 180 are preferably attached to the second panel 176 by a suitable adhesive or fastening device. An actuating device 222 is coupled to the outer ends of the flaps 188 adjacent the coupling tabs 198. The actuating device 222 extends between the first and second panels toward the center aperture 204 and is guided along the convex edges 208 and 210 to the aperture 218. The actuating device 222 extends through the aperture 218 and extends beyond the edge 220 of the panels 174 and 176 a sufficient distance to be gripped by a user. In the embodiment illustrated, the actuating device 222 is a flexible cord having each end attached to a respective end of the first panel. A suitable clamping device 224 is provided on the actuating device 222 to limit the movement of the actuating device through the aperture 218. The clamping device 224 can be a spring biased clamp capable of gripping the actuating device and preventing the actuating device from retracting in the immobilizing device 170.

A top panel 226 is positioned over the center panel 180 to cover the aperture 204. Preferably, the top panel 226 is dimensioned to completely cover the center panel 180 and is attached thereto by a suitable adhesive or other fastening device. Generally, the top panel 226 is a flexible cushioning foam for supporting a patient's head, although other materials can be used.

The cervical immobilizing device 170 is used in a similar manner to the previous embodiments. As in the previous embodiments, the device 170 is attached to a rigid backboard by adhesive strips 228 on the bottom side of the second panel 176. A patient's head is placed on the top panel 226 with the actuating device 222 extending away from the patient's body. The actuating device 222 is pulled away from the center panel 180 which draws the outer edges of the flaps 188 inwardly toward the center panel. As the actuating device pulls the outer edges of the flaps 188 toward the center panel, the flaps 188 fold along the fold lines 190 and 192 to an upright position as shown in FIG. 18.

The actuating device 222 pulls the outer edges of the flaps 188 to an upright position in a symmetrical fashion to avoid or reduce movement of the patient's head during the use of the device. The coupling tabs 198 slide along the second panel 176 and are received in one of the slots 216 to lock the outer panel 196 in a fixed position. The different slots 216 allow selective adjustment of the position of the coupling tabs 198 to accommodate different patients. Although four slots are shown for each of the coupling tabs 198, it will be appreciated that additional or fewer slots can be used as needed to accommodate different size patients.

The actuator device 222 is pulled to a position where the inner panels 194 contact the patient's head and conforms to the shape of the patient's head and the coupling tab 198 is positioned in the appropriate slot 216. The suitable strap or tape is then placed across the forehead of the patient and attached to the immobilizing device 170 to secure the patient's head in a fixed position. The clamping device 224 can be slid along the actuating device 222 until it engages the edge of the device 170 to prevent the actuating device 222 from retracting into the device and allowing the flaps 188 to unfold or return to their original position. In further embodiments, the arms 188 can be moved individually by manually pushing the arms inwardly to the folded upright position and locked in place by inserting the tabs 198 into a selected slot 216. In this embodiment, the actuator device can be eliminated.

Figure 19:
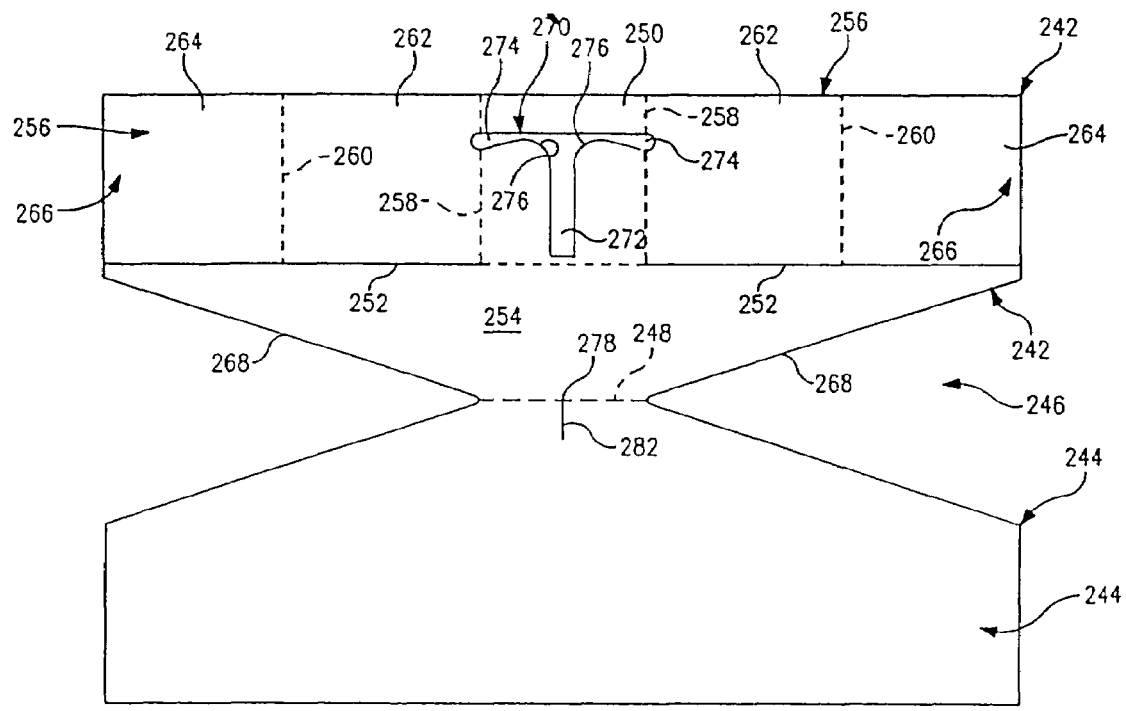
FIG. 19 is a top view of a blank in a further embodiment of the invention.
Figure 20:
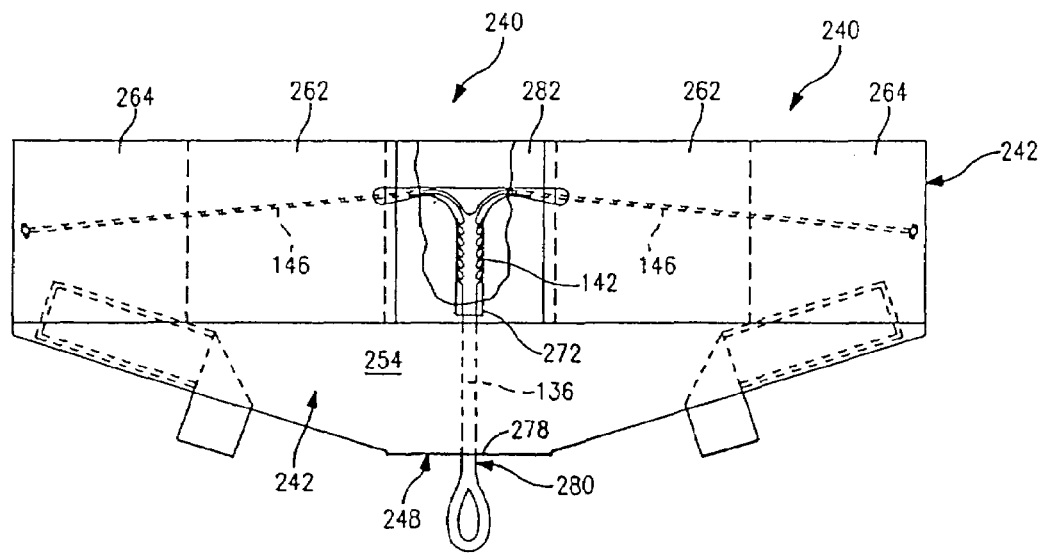
FIG. 20 is a top plan view of the cervical immobilization device made from the blank of FIG. 19.

In a further embodiment, the cervical immobilizing device 240 is formed from two superimposed panels 242 and 244 as shown in FIGS. 19 and 20. The immobilizing device 240 can be formed from separate panels that are bonded together. In the illustrated embodiment, the device 240 is made from a fold blank 246 of cardboard or other material as shown in FIG. 19. The blank 240 includes the first panel 242 and the second panel 244 coupled together along a fold line 248. The first panel 242 and the second panel 244 are substantially the same shape and size.

The first panel 242 includes a center panel 250 and cut lines 252 to form a top portion 254 and arms 256. Each arm 256 is coupled to the side edges of the center panel 250 by a fold line 258. The arms 256 include an intermediate fold line 260 to define an inner panel 262 and outer panel 264. An aperture 266 is formed in each of the outer panels 264 adjacent the outermost edges.

The top portion 254 of panel 242 has a longitudinal dimension equal to the combined longitudinal dimension of the arms 256 and the center panel 250. The top portion has a generally truncated triangular shape with side edges 268 converging toward the fold line 248. A slit 278 is formed along the fold line 248.

The center panel 250 includes a generally T-shaped aperture 270 having a base portion 272 extending in the direction of the fold line 248 and a pair of arm portions 274. As shown in FIG. 19, arm portions 274 have a curved portion 276. The arm portions 274 have a length to extend a slight distance past the fold lines 258 into the inner panels 262.

The cervical immobilizing device 240 is formed by folding the blank 246 along the fold line 248 and attaching the panels 242 and 246 together. Generally, the top portion 254 and the center panel 246 are attached to the second panel 244 by a suitable adhesive. The arms 256, as in the previous embodiments, are movable with respect to the second panel 244.

An actuating device 280 is attached to each end of the arms by inserting the free end through the apertures 266. The actuator device 280 is substantially the same as in the previous embodiments so identical elements are identified by the same reference numbers. The end of the actuator fed through a transverse slit 282 in the second panel 244 and positioned in the longitudinal slit as shown in FIG. 20. The flexible legs of the actuator device extend around the curved portions 276 of the aperture 270, which serve as a guide for the flexible legs. A flexible cushion or pad 284 is generally attached to the center panel to cover the aperture in the center panel.

The cervical immobilizing device 240 is used in a similar manner as the previous embodiments. The actuator device 280 is pulled by the user so that the arms 256 are moved to a folded upright position as in the previous embodiments. The teeth of the actuator device are pulled through the slit 282 to engage the walls of the slit 278 and lock the arms in the folded position.

Several embodiments have been chosen to illustrate the invention. It will be appreciated by those skilled in the art that various other modifications and embodiments can be constructed without departing from the various features of the invention. For example, the actuating device in each of the illustrated embodiments is a flexible member that is pulled away from the device to pull the outer ends of the support arms of the device toward the patient's head to a locked position. In further embodiments, the actuator device can be an assembly of flexible or rigid components or levers that can be either pushed or pulled to draw the arms from the flat position to the upright position for engaging the patient's head. In a further embodiment, the actuator device can include a pair of rigid levers extending from the outer ends of the arms and coupled together by a pivot mechanism at the center of the device. An arm or lever can be attached to the pivot device that can be pulled or pushed causing a scissor-like action of the rigid members to pull the outer ends of the flaps toward the center of the device. In a similar manner, the locking device can be other arrangements for fixing the position of the arms in the folded position during use.

What is claimed is:

1. A cervical immobilizing device, comprising:
a base having first and second ends, a front edge and a rear edge;
a cervical immobilizing member coupled to said base and being foldable from a first position to a second folded position for engaging a patient's head, said cervical immobilizing member including a center portion attached to said base and including a pair of movable arms for engaging said patient's head when in said second position, said arms having a first pivotal coupling for coupling an inner edge of said arms to said center portion and an outer edge facing outwardly toward a respective end of said base, said center portion comprises a center panel and each said foldable arms include a second pivotal coupling spaced from said first pivotal coupling to define an inner panel adjacent said center panel and an outer panel;
an actuating device coupled to each of said outer edges of said arms, said actuating device being disposed for simultaneously and substantially symmetrically sliding said outer edges of said arms from said first position toward said center panel to said second folded position for supporting said patient's head; and
a locking device for locking said actuating device wherein said locking device is a member selected from the group consisting of cinching device, ratcheting device, a clamping device, and combinations thereof.

2. The immobilizing device of claim 1, wherein said locking device is a member selected from the group consisting of a latch, ratchet and pawl structures, pin and stopper structures, raised surfaces with complementary receiving apertures, a releasable clamp, hook and loop fabric, releasable adhesive, friction devices, and combinations thereof.

3. The immobilizing device of claim 1, wherein said locking device is a member selected from the group consisting of a latch, ratchet and pawl structures, pin and stopper structures, raised surfaces with complementary receiving apertures, a releasable clamp, hook and loop fabric, releasable adhesive, friction devices, and combinations thereof.

4. The immobilizing device of claim 3, wherein said locking device is a latch, said latch has at least one protrusion, said latch is pressed into a fixed locking position whereby said protrusion engages said actuator device.

5. The immobilizing device of claim 4, wherein said latch in said fixed, locked position frictionally engages said actuator device.

6. The immobilizing device of claim 5, wherein said latch has at least one protrusion, said protrusion engages a complementary receiving means in said actuator device.

7. The immobilizing device of claim 6, wherein said complementary receiving means in said actuator device is a slot between two complementary teeth on said actuator device.

8. The immobilizing device of claim 3, wherein said locking device is a ratchet and pawl structure, said ratchet and pawl structure has at least one ratchet and at least one complementary pawl.

9. The immobilizing device of claim 8, wherein at least one said ratchet is on at least one side of said actuator device and a tension device pushes said pawl into said ratchet.

10. The immobilizing device of claim 3, wherein said locking device is a pin and stopper structure, said pin and stopper structure has at least one pin and at least one complementary stopper.

11. The immobilizing device of claim 10, wherein at least one said pin is on at least one side of said actuator device and a tension device pushes said pin into said complementary stopper.

12. The immobilizing device of claim 3, wherein said locking device is hook and loop fabric.

13. The immobilizing device of claim 3, wherein said locking device is a clamp.

14. A cervical immobilizing device, comprising
a base having first and second ends, a front edge and a rear edge, said base having a first longitudinal slot extending from said first end toward a center portion of said base and a second longitudinal slot extending from said second end toward said center portion of said base;
a cervical immobilizing member having a center panel attached to said center portion of said base, a first arm having an inner end coupled to a first edge of said center panel and an outer end spaced from said inner end, and a second arm having an inner end coupled to a second side of said center panel and an outer end spaced from said inner end, said first arm having a first coupling member for sliding engagement with said first slot and for coupling said first arm to said base, and said second arm having a second coupling member for sliding engagement with said second slot and for coupling said second arm to said base, said first and second arms being foldable from a first substantially flat position to a second folded, upright position;
a locking device for locking said first and second arms in said folded, upright position, said locking device is a member selected from the group consisting of cinching device, ratcheting device, a clamping device, and combinations thereof;
an actuating device coupled to said first and second arms for simultaneously and substantially symmetrically sliding said outer ends of said first and second arms inwardly toward said center panel to fold each of said arms to said second folded upright position having a substantially inverted V-shaped configuration to engage and support a patient's head; and
a guide member positioned on a bottom face of said base for guiding said actuating device and having a first end substantially aligned inwardly with respect to said tabs, an elongated slot having guiding surfaces extending inwardly from said first end toward a second end of said guide member, wherein said actuating member passes through said slot from said first end to said second end, whereby pulling said actuating device through said slot pulls the ends of said arms toward said center panel to said folded position.

15. A cervical immobilizing device, comprising a base having first and second ends, a front edge and a rear edge, said base having a first longitudinal slot extending from said first end toward a center portion of said base and a second longitudinal slot extending from said second end toward said center portion of said base;

a cervical immobilizing member having a center panel attached to said center portion of said base, a first arm having an inner end coupled to a first edge of said center panel and an outer end spaced from said inner end, and a second arm having an inner end coupled to a second side of said center panel and an outer end spaced from said inner end, said first arm having a first coupling member for sliding engagement with said first slot and for coupling said first arm to said base, and said second arm having a second coupling member for sliding engagement with said second slot and for coupling said second arm to said base, said first and second arms being foldable from a first substantially flat position to a second folded, upright position;

a locking device for locking said first and second arms in said folded, upright position, said locking device is a member selected from the group consisting of cinching device, ratcheting device, a clamping device, and combinations thereof; and an actuating device coupled to said first and second arms for simultaneously and substantially symmetrically sliding said outer ends of said first and second arms inwardly toward said center panel to fold each of said arms to said second folded upright position having a substantially inverted V-shaped configuration to engage and support a patient's head;

wherein said actuating member includes a body portion having a plurality of teeth and a pair of flexible legs, each of said legs being coupled to a respective arm of said immobilizing member, and wherein said immobilizing device includes an aperture, said body portion of said actuating member passing through said aperture whereby the teeth of said body portion engage a side wall of said aperture to lock said actuating member and lock said arms in said folded position.

* * * * *